(12) United States Patent
Biberger

(10) Patent No.: US 8,459,100 B2
(45) Date of Patent: Jun. 11, 2013

(54) IN-SITU WATER ANALYSIS METHOD AND SYSTEM

(75) Inventor: Maximilian A. Biberger, Scottsdale, AZ (US)

(73) Assignee: Hitek Aqua Systems, Tempe, AZ (US)

( * ) Notice: Subject to any disclaimer, the term of this patent is extended or adjusted under 35 U.S.C. 154(b) by 736 days.

(21) Appl. No.: 12/728,055

(22) Filed: Mar. 19, 2010

(65) Prior Publication Data

US 2010/0188236 A1 Jul. 29, 2010

Related U.S. Application Data

(63) Continuation of application No. 11/165,478, filed on Jun. 22, 2005, now Pat. No. 7,681,436.

(51) Int. Cl.
*G01N 33/18* (2006.01)

(52) U.S. Cl.
USPC .......... 73/53.01; 73/61.41; 73/61.51; 210/85; 340/539.22

(58) Field of Classification Search
USPC ............ 4/490; 73/53.01, 61.41–61.51, 61.61, 73/61.71; 210/85–95; 340/539.22, 539.24, 340/539.26; 374/156
See application file for complete search history.

(56) References Cited

U.S. PATENT DOCUMENTS

| | | | |
|---|---|---|---|
| D138,325 S | 7/1944 | Pool | D91/1 |
| 3,162,470 A | 12/1964 | Davidson et al. | 285/86 |
| D242,618 S | 12/1976 | Milo | D23/19 |
| D254,266 S | 2/1980 | Tableriou | D23/40 |
| 4,435,095 A | 3/1984 | Jones et al. | 374/194 |
| 4,510,487 A | 4/1985 | Wolfe et al. | 340/566 |
| 4,781,810 A | 11/1988 | Tucker | 204/228 |
| 4,900,432 A | 2/1990 | Arnold et al. | 210/91 |
| 4,940,946 A | 7/1990 | Nazaryan | 324/438 |
| 5,055,183 A | 10/1991 | Buchan | 210/85 |
| 5,115,222 A | 5/1992 | Peralta et al. | 340/573 |
| 5,124,960 A | 6/1992 | Miller et al. | 368/278 |
| 5,152,610 A | 10/1992 | Hallett | 374/156 |
| 5,169,236 A | 12/1992 | Iest | 374/156 |
| 5,189,350 A | 2/1993 | Mallett | 318/434 |
| 5,422,014 A | 6/1995 | Allen et al. | 210/743 |
| 5,518,635 A | 5/1996 | Kohlman | 210/749 |
| D371,824 S | 7/1996 | Price et al. | D23/208 |

(Continued)

FOREIGN PATENT DOCUMENTS

| | | |
|---|---|---|
| DE | 199 21 436 A1 | 11/2000 |
| EP | 821514 A1 | 1/1998 |
| WO | WO 03/087501 A1 | 10/2003 |
| WO | WO 03/091668 A2 | 11/2003 |

OTHER PUBLICATIONS

Griffin, William R., "Maintaining Swimming Pools, Spas, Whirlpool Tubs, and Saunas", Jan. 2001, Cleaning Consultant Services, Inc., Seattle WA, 4 pages.

(Continued)

*Primary Examiner* — David Rogers
(74) *Attorney, Agent, or Firm* — Haverstock & Owens, LLP

(57) ABSTRACT

An automatic system for monitoring chemistry information for a body of water comprises a sensor for determining chemistry information, a microprocessor for processing chemistry information, and a housing coupled to at least one of the sensor and the microprocessor. Preferably the housing is floatable or mountable. The method of providing chemistry information of a body of water comprising the steps of obtaining a sample of the body of water and determining chemistry information.

24 Claims, 17 Drawing Sheets

U.S. PATENT DOCUMENTS

| | | | | |
|---|---|---|---|---|
| 5,681,110 | A | 10/1997 | Burzacchi | 374/156 |
| 5,788,826 | A | 8/1998 | Nyberg | 204/536 |
| 5,996,138 | A | 12/1999 | Kentch | 4/508 |
| 6,113,858 | A | 9/2000 | Tang et al. | 422/82.09 |
| D432,206 | S | 10/2000 | Stoltz et al. | D23/209 |
| D439,313 | S | 3/2001 | Wey et al. | D23/236 |
| 6,223,359 | B1 | 5/2001 | Oltmanns et al. | 4/508 |
| 6,225,900 | B1 | 5/2001 | Keon et al. | 340/539 |
| 6,228,272 | B1 | 5/2001 | Gola | 210/742 |
| 6,238,553 | B1 | 5/2001 | Lin | 210/94 |
| 6,294,086 | B1 | 9/2001 | Reeves | 210/198.1 |
| 6,309,538 | B1 | 10/2001 | Khan | 210/85 |
| 6,340,431 | B2 | 1/2002 | Khan | 210/85 |
| 6,476,721 | B1 | 11/2002 | Diebold | 340/573.6 |
| 6,579,446 | B1 | 6/2003 | Teran et al. | 210/85 |
| 6,653,842 | B2 * | 11/2003 | Mosley et al. | 324/446 |
| 6,697,706 | B2 | 2/2004 | Gardner, Jr. | 700/244 |
| 6,713,298 | B2 | 3/2004 | McDevitt et al. | 435/287.8 |
| D489,431 | S | 5/2004 | Antunez | D23/236 |
| 6,792,956 | B2 | 9/2004 | Bredo et al. | 134/22.18 |
| 6,958,693 | B2 | 10/2005 | Rothgeb et al. | 340/539.22 |
| 7,037,038 | B1 | 5/2006 | Haski et al. | 405/60 |
| D526,382 | S | 8/2006 | Thompson | D23/208 |
| D537,913 | S | 3/2007 | Biberger et al. | D23/208 |
| D559,943 | S | 1/2008 | Mercer | D23/208 |
| 2001/0045380 | A1 | 11/2001 | Khan | 210/85 |
| 2002/0035403 | A1 | 3/2002 | Clark et al. | 700/65 |
| 2002/0195403 | A1 | 12/2002 | Takeda et al. | |
| 2003/0227394 | A1 | 12/2003 | Rothgeb et al. | 340/870.19 |
| 2004/0031329 | A1 | 2/2004 | Carpenter et al. | 73/861.19 |
| 2004/0066313 | A1 | 4/2004 | Ong et al. | 340/870.11 |
| 2004/0208499 | A1 | 10/2004 | Grober et al. | 396/428 |
| 2005/0220169 | A1 | 10/2005 | McGowan-Scanlon | 374/156 |
| 2005/0225766 | A1 | 10/2005 | Hansen et al. | 356/436 |
| 2005/0279677 | A1 | 12/2005 | Lin | 210/96.1 |
| 2006/0096927 | A1 | 5/2006 | Clukies | 210/691 |

OTHER PUBLICATIONS

"Water Chemistry for Swimming Pools," Pool Water Chemistry, North Carolina Department of Environment and Natural Resources, available on the Internet at <http://web-archive.org/>, Dec. 19, 2002, 12 pgs.

United States Patent and Trademark Office, Office Action, mailed Dec. 22, 2006, U.S. Appl. No. 11/165,478, filed Jun. 22, 2005, First Named Inventor: Maximilian A. Biberger, 4 pages.

United States Patent and Trademark Office, Office Action, mailed Jul. 19, 2007, U.S. Appl. No. 11/165,478, filed Jun. 22, 2005, First Named Inventor: Maximilian A. Biberger, 9 pages.

United States Patent and Trademark Office, Office Action, mailed Feb. 4, 2008, U.S. Appl. No. 11/165,478, filed Jun. 22, 2005, First Named Inventor: Maximilian A. Biberger, 10 pages.

United States Patent and Trademark Office, Advisory Action, mailed Apr. 24, 2008, U.S. Appl. No. 11/165,478, filed Jun. 22, 2005, First Named Inventor: Maximilian A. Biberger, 3 pages.

United States Patent and Trademark Office, Office Action, mailed Jun. 18, 2008, U.S. Appl. No. 11/165,478, filed Jun. 22, 2005, First Named Inventor: Maximilian A. Biberger, 9 pages.

United States Patent and Trademark Office, Office Action, mailed Dec. 5, 2008, U.S. Appl. No. 11/165,478, filed Jun. 22, 2005, First Named Inventor: Maximilian A. Biberger, 10 pages.

United States Patent and Trademark Office, Office Action, mailed Jun. 19, 2009, U.S. Appl. No. 11/165,478, filed Jun. 22, 2005, First Named Inventor: Maximilian A. Biberger, 10 pages.

United States Patent and Trademark Office, Notice of Allowance and Fee(s) Due, mailed Nov. 30, 2009, U.S. Appl. No. 11/165,478, filed Jun. 22, 2005, First Named Inventor: Maximilian A. Biberger, 6 pages.

United States Patent and Trademark Office, Office Action, mailed Sep. 10, 2007, U.S. Appl. No. 11/710,077, filed Feb. 23, 2007, First Named Inventor: Maximilian A. Biberger, 10 pages.

United States Patent and Trademark Office, Office Action, mailed Feb. 1, 2008, U.S. Appl. No. 11/710,077, filed Feb. 23, 2007, First Named Inventor: Maximilian A. Biberger, 10 pages.

United States Patent and Trademark Office, Advisory Action, mailed May 1, 2008, U.S. Appl. No. 11/710,077, filed Feb. 23, 2007, First Named Inventor: Maximilian A. Biberger, 3 pages.

United States Patent and Trademark Office, Office Action, mailed Aug. 25, 2008, U.S. Appl. No. 11/710,077, filed Feb. 23, 2007, First Named Inventor: Maximilian A. Biberger, 11 pages.

United States Patent and Trademark Office, Office Action, mailed Apr. 6, 2009, U.S. Appl. No. 11/710,077, filed Feb. 23, 2007, First Named Inventor: Maximilian A. Biberger, 12 pages.

United States Patent and Trademark Office, Advisory Action, mailed Jul. 10, 2009, U.S. Appl. No. 11/710,077, filed Feb. 23, 2007, First Named Inventor: Maximilian A. Biberger, 3 pages.

United States Patent and Trademark Office, Office Action, mailed Sep. 2, 2009, U.S. Appl. No. 11/710,077, filed Feb. 23, 2007, First Named Inventor: Maximilian A. Biberger, 13 pages.

United States Patent and Trademark Office, Office Action, mailed Jan. 27, 2010, U.S. Appl. No. 11/710,077, filed Feb. 23, 2007, First Named Inventor: Maximilian A. Biberger, 15 pages.

United States Patent and Trademark Office, Notice of Allowance and Fee(s) Due, mailed Mar. 8, 2010, U.S. Appl. No. 11/710,077, filed Feb. 23, 2007, First Named Inventor: Maximilian A. Biberger, 6 pages.

United States Patent and Trademark Office, Office Action, mailed Aug. 1, 2007, U.S. Appl. No. 11/477701, filed Jun. 28, 2006, First Named Inventor: Maximilian A. Biberger, 7 pages.

United States Patent and Trademark Office, Notice of Allowance and Fee(s) Due, mailed Feb. 1, 2008, U.S. Appl. No. 11/477,701, filed Jun. 28, 2006, First Named Inventor: Maximilian A. Biberger, 5 pages.

* cited by examiner

IN-SITU WATER ANALYSIS METHOD AND SYSTEM

CROSS-REFERENCE TO RELATED APPLICATIONS

The present application is a continuation of co-pending U.S. patent application Ser. No. 11/165,478, filed on Jun. 22, 2005, and entitled "IN-SITU WATER ANALYSIS METHOD AND SYSTEM," which is hereby incorporated by reference in its entirety.

FIELD OF THE INVENTION

The present invention relates generally to the field of water analysis. More specifically, the present invention relates to the field of automated water chemistry analysis.

BACKGROUND OF THE INVENTION

For owners of recreational aquatic facilities, such as pools, spas, and hot tubs, water chemistry must be properly maintained to deflect the hazards associated with water not properly balanced. If the chemistry of a pool is even slightly off, for instance, a serious health hazard can be posed to users. Also, water that is not properly balanced can result in a quick deterioration of an aquatic facility, resulting in expensive rehabilitation costs.

Presently, water chemistry can be checked by chemistry kits, laboratory runs, and maintenance service calls. Although chemistry kits are typically less expensive than maintenance service calls, most chemistry kits are messy, complicated, and are not user-friendly. Even if one knows how to properly use a chemistry kit, that individual may be uncertain of the results, thereby necessitating a double check of the water chemistry through a laboratory run such as to a swimming pool supply store.

A laboratory run requires the taking of a sample of water for a chemistry laboratory to analyze. Traveling to and from a laboratory with the sample during normal business hours is inconvenient. Further the result is obtained after a significant lag time has elapsed. Moreover, the analysis of water chemistry and an evaluation of the amount of additives to remedy any perceived imbalance is a function of water temperature. It is almost certain that the temperature of the sample will change in transit to the laboratory. Furthermore, once the results are received from a laboratory, water chemistry may have changed and as a consequence, one may be relying on an inaccurate water chemistry reading. For those who use chemistry kits and laboratory runs, both options also do not address the problem of physically adding chemicals to the water, which equate to an added inconvenience of releasing messy chemicals, without much assurance that the correct amount of chemicals are being released at the proper time. Overall, chemistry kits, laboratory runs, and adding chemicals on a do-it-yourself basis can be inaccurate, labor-intensive and time-consuming.

In contrast, maintenance service calls are expensive and inconvenient. Although service calls are typically conducted at regular intervals, sometimes maintenance service personnel are unavailable when their services are most needed, such as after a rain storm or before a pool party. Also, some maintenance service personnel are unreliable and/or careless in their methodology, forcing one to double check water chemistry by using a chemistry kit or a laboratory run. Finally, such service calls can be conducted by a variety of maintenance personnel, thereby increasing the likelihood of human error in monitoring and balancing water chemistry.

What is needed is a safe, convenient, user-friendly automated system for monitoring water chemistry.

What is needed is an efficient, time-sensitive automated system for both monitoring water chemistry and adding necessary chemicals to balance the water.

What is needed is a reliable automated method for monitoring water chemistry.

What is needed is a secure, dependable automated method for both monitoring water chemistry and adding appropriate chemicals to maintain the balance of a body of water.

SUMMARY OF THE INVENTION

The present invention is a method and system for monitoring water chemistry and appropriately metering chemicals to balance water. The method and system are user-friendly and automated, thereby alleviating concerns about safety, accuracy, and timeliness of the chemistry reading. The method and system can be utilized for a body of water, including but not limited to, a spa, a pool, a hot tub, a whirlpool tub, and the like.

One aspect of the present invention includes an automatic system for monitoring chemistry information for a body of water. The system comprises a sensor for determining chemistry information, a control circuit coupled to the sensor for processing chemistry information, and a housing coupled to one of the sensor and the control circuit. Preferably, the housing of the automatic system is floatable. Alternatively the housing is mountable.

Another aspect of the present invention includes an automatic system for monitoring chemistry information for a body of water and introducing chemicals into the body of water. The system comprises a pump system for collecting a sample of the body of water, a sensor coupled to the pump system for determining chemistry information based on the sample, and a control circuit coupled to the sensor for processing chemistry information. The control circuit further comprises an instruction which instructs the control circuit to compare a programmable threshold of chemistry information to chemistry information sensed from the sample. The system further comprises a chemical storage unit coupled to the pump system and the control circuit configured to release a chemical into the body of water upon command, a safety element coupled to the control circuit or the sensor and configured to indicate when water is unsafe or out of the desired range of specification, and a housing coupled to one of the pump system, the sensor, the control circuit, the chemical storage unit, and the safety element. The control circuit provides one or more signals to the safety element to alert when the water is unsafe once the programmable threshold is met. Preferably, the housing of the automatic system is floatable. Alternatively, the housing is mountable.

A further aspect of the present invention includes a mountable automatic system for monitoring chemistry information of a body of water having a cover and introducing chemicals into the body of water. The system comprises a pump system for collecting a sample of the body of water. A sensor is coupled to the pump system for determining chemistry information of the sample. A control circuit is coupled to the sensor for processing chemistry information. A chemical storage unit is coupled to the pump system and the control circuit and is configured to release a chemical into the body of water upon command. An antenna is coupled to at least one of the control circuit and the sensor. A mountable housing is coupled to at least one of the pump system, the sensor, the control circuit, the chemical storage unit, and the antenna.

The antenna extends from the system. The control circuit further comprises a program which instructs the control circuit to compare a programmable threshold of chemistry information to chemistry information sensed from the sample. The control circuit transmits one or more signals via the antenna to alert a remote location when the body of water is either unsafe or fails to meet predetermined requirements once the programmable threshold has been met. Preferably, the body of water is a swimming pool. Alternatively, the body of water can be one of a hot tub and a spa.

Yet another aspect of the present invention includes a method of automatically monitoring chemistry information of a body of water. The method comprises the steps of determining chemistry information based on a sample obtained from the body of water and processing chemistry information.

A further aspect of the present invention includes an automatic system for monitoring chemistry information of a body of water. The system comprises means for determining chemistry information based on a sample obtained from the body of water and means for processing chemistry information.

Another aspect of the present invention includes an automatic sensor for providing chemistry information of a body of water. The sensor is configured to couple to a retrieval element and a housing.

Yet another aspect of the present invention includes a method of providing chemistry information of a body of water. The method comprises the steps of obtaining a sample of the body of water and determining chemistry information.

Another aspect of the present invention includes an automatic system for monitoring chemistry information for hot tub water. The automatic system comprises a retrieval element for obtaining a sample from hot tub water, a sensor coupled to the retrieval element for determining chemistry information, a display coupled to the sensor for displaying chemistry information, and a housing coupled to one of the retrieval element, the sensor, and the display.

DETAILED DESCRIPTION OF THE INVENTION

In the past, it has been difficult to obtain accurate and timely chemistry readings of bodies of water. In particular, bodies of water, such as pools, spas, and hot tubs, have been at risk of calcium deposits and eroding surfaces due to water being "out of balance". Keeping water in balance oftentimes requires some knowledge about water chemistry, which many people lack. Also, maintaining the proper water balance requires some labor typically, including testing the water and making additions of chemicals and proper water treatments. If water is out of balance, it could result in staining, calcium deposits on the surface or tile, and eroding surfaces due to leeching of calcium carbonate. Also, if the water is too acidic, it may damage or even completely destroy water equipment, such as the water heating element.

The present invention solves all of these problems in a simple, user-friendly method and system to monitor water chemistry and to add proper chemicals, based on current chemistry and temperature information of the body of water. Although preferably the present invention is used for recreational aquatic facilities, such as pools, spas, and hot tubs, the present invention is also intended to be used for other bodies of water, including but not limited to, a bath, a fountain, a whirlpool bath, and the like. The present invention further allows for chemistry information to be ascertained from a body of water at any given moment, regardless of weather conditions, the number of people in the water, and the time of day. The chemistry information can even be monitored while people are present in the water. Furthermore, the present invention adds the benefits of safety and convenience. It frees one from having uncertainty over the accuracy of chemistry information for the body of water. The present invention allows for continuous or repeated monitoring of chemistry information. Also, the present invention eliminates the necessity of having to double-check chemistry information readings because its automatic capabilities lessen the possibility of human error. Thus, the invention does not require for individuals to use chemistry kits, rely on unreliable maintenance personnel, or waste time making laboratory runs. Instead, the present invention is an all-inclusive automatic package that addresses virtually all the problems associated with the monitoring and maintenance of water balance, with none of the hassles and problems of chemistry kits, fixed maintenance calls, and laboratory runs. Moreover, because the analysis takes place in site, the actual temperature of the water is also properly determined and taken into account.

Figure 1:
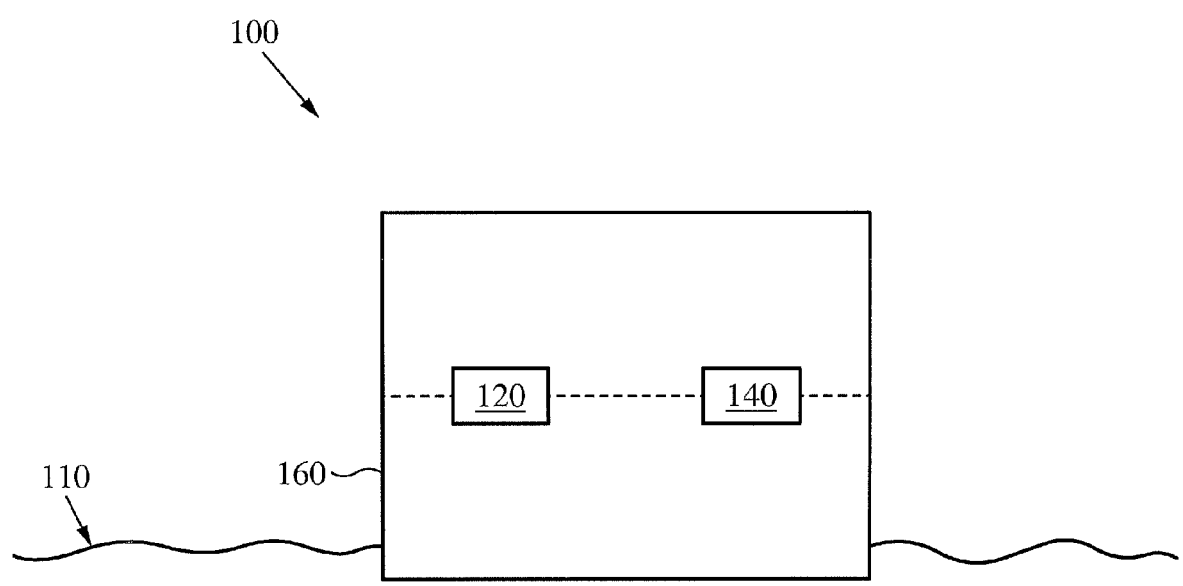
FIG. 1 is a schematic drawing of a preferred embodiment of the present invention for a floatable automatic system for monitoring chemistry information for a body of water.

Referring now to FIG. 1, a preferred embodiment of the present invention includes an automatic system 100 for monitoring chemistry information of a body of water 110. The system 100 comprises three elements, namely a sensor 120, a control circuit 140, and a housing 160. Preferably, the housing 160 is a floatable housing, thus making the system a floatable automatic system 100, as shown in FIG. 1. It will be apparent to those skilled in the art that the housing 160 can be of any shape, size, and color tailored to the environment surrounding the system 100. The sensor 120 determines chemistry information for the body of water 110. It will be appreciated by those skilled in the art that the type and actual number of sensors within a particular automatic system 100 depends upon the application of the present invention. Furthermore, it will be apparent to those skilled in the art that the housing 160 can be a mountable housing, rather than a floatable housing. This particular alternative embodiment encompassing a system with a mountable housing will be specifically described later. The sensor 120 is coupled to the housing 160 such that the sensor 120 is in operative communication with the body of water 110. For example, the sensor 120 can be mounted external to the housing 160. More preferably, the housing 160 includes an aperture (not shown) containing the sensor 120 wherein a portion of the body of water 110 can freely enter and exit the aperture.

It will be apparent to those of ordinary skill in the art that the control circuit 140 can comprise a power supply, buffer circuit to convert signals generated by the sensor 120 to levels suitable for the control circuit 140 in programmable memory to store programs, and dynamic memory to hold sensed chemistry information and receive/transmit circuits to communicate information. A microprocessor, CPU, microcontroller or specially designed processor including an ASIC, PLA, PAL, PSA among other digital circuits can be coupled to function and control the control circuit 140.

Referring still to FIG. 1, the control circuit 140 is coupled to the sensor 120, with the control circuit 140 configured to process electronic signals generated by the sensor 120 in response to sensed chemistry information for the body of water 110. The housing 160 is coupled to at least one of the sensor 120 and the control circuit 140. As shown in FIG. 1, for the preferred embodiment of the present invention, the system 100 is configured to remain afloat in the body of water 110 for long periods of time without human supervision. The control circuit 140 further compares chemistry information for the body of water 110, which was determined by the sensor 120, to a programmable threshold. The programmable threshold represents an acceptable value of chemistry information for the body of water 110. Preferably, the programmable threshold can be a minimum or a maximum value of chemistry information for the body of water 110. Furthermore, the programmable threshold can be adjusted and the system 100 can provide suggested thresholds based on parameters of the body of water 110. Thus, the system 100 can give suggested thresholds after it is programmed with the dimensions, volume, and type of body of water 110 being monitored by the system 100. Also, the programmable threshold is useful given that when the threshold is met, the system 100 can alert that the threshold has been reached and an action must be performed. For instance, the system 100 can alert that the body of water 110 contains too much chlorine or the water pH level is dangerously acidic. Hence, the system 100 can detect if the programmable threshold has been met and the system 100 can indicate when the body of water 110 is off balance and/or unsafe.

Chemistry information monitored by the floatable system 100 can be at least one of alkalinity, pH level, temperature, calcium hardness, total hardness, dissolved solids, a sanitizer (including, but not limited to, chlorine and bromine) of the body of water 110 and a combination of at least two thereof. However, it will be appreciated by those skilled in the art that chemistry information is not limited to the list noted above and can include chemistry information about any component for the body of water 110. Furthermore, in the preferred embodiment, the floatable system 100 can monitor more than one chemical component for the body of water 110 at a time. Preferably, the floatable system 100 is configured to monitor chemistry information for the body of water 110 continually while the floatable system 100 is powered on. Preferably, the body of water 110 is at least one of a spa, a pool, a hot tub, a bath, a fountain, and a whirlpool bath. It will be appreciated by those skilled in the art that the present invention can also be utilized to monitor chemistry information for any body of liquid. While it is possible to include chemical reservoirs and chemical delivery systems in an automatic system that floats, generally the volume of chemicals needed for maintaining balance in a pool, hot tub or spa are sufficiently large that storing such chemicals in a floating device can diminish or interfere with enjoyment of the pool, hot tub or spa.

Figure 3A:
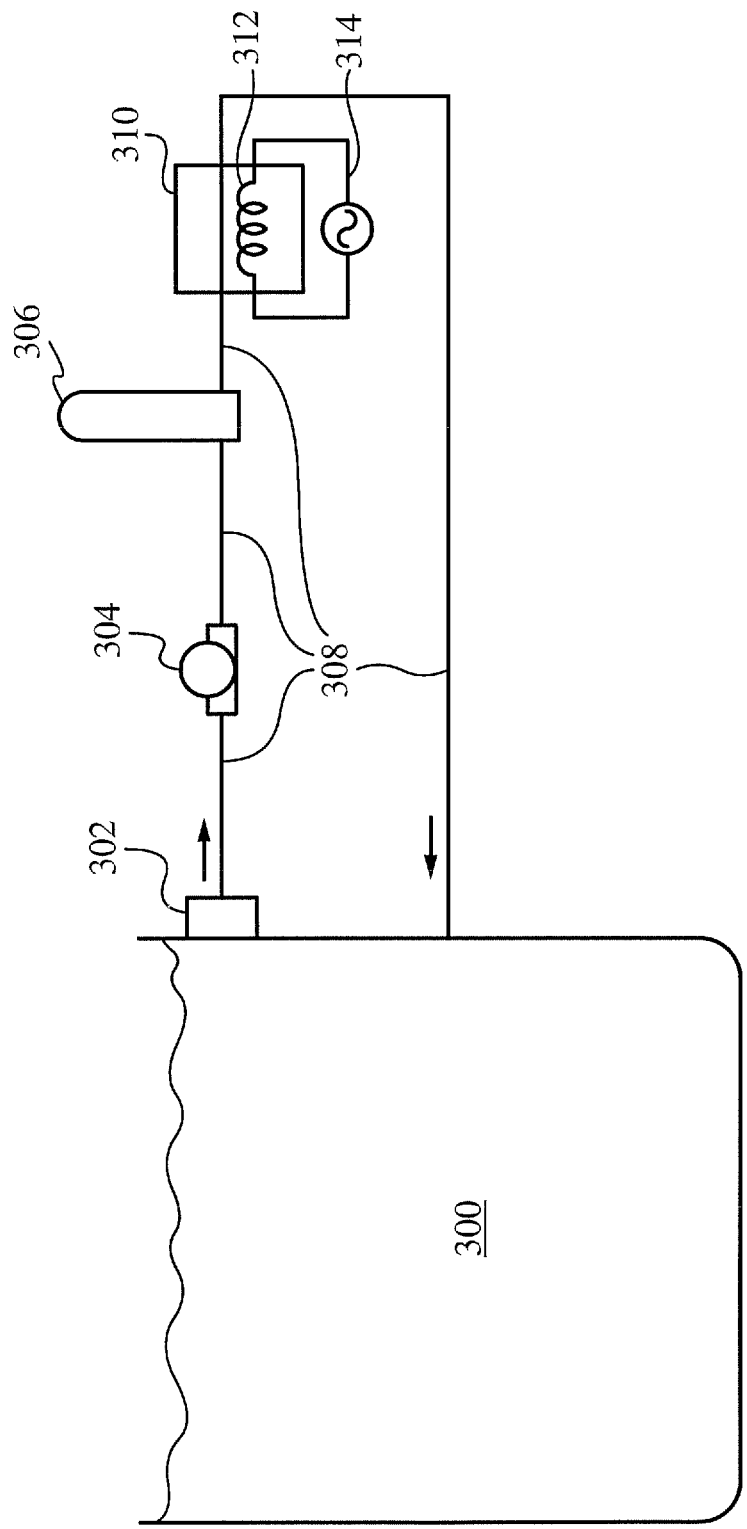
FIG. 3A is a schematic drawing of a conventional pool, hot tub or spa, including a skimmer, a filter, a heater and a pump.

A conventional pool, hot tub or spa 300 such as schematically shown in FIG. 3A generally includes a skimmer 302 to collect leaves and other debris in the usual manner. A pump 304 draws water through piping 308 from the skimmer 302 and delivers it to a filter 306. Owing to the pressure of the pump 304, the water passes through the filter 306 and then through an optional heater 310. The heater 310 shown in FIG. 3A heats the water using a coil 312 powered by an alternating current source 314 such as from the electric power grid. Other heating means are also well known and include solar collectors and natural gas flame heaters. The water is returned to the pool, hot tub or spa 300 under pressure from the pump 304. The precise sequence of the elements shown in FIG. 3A can be altered.

Figure 2:
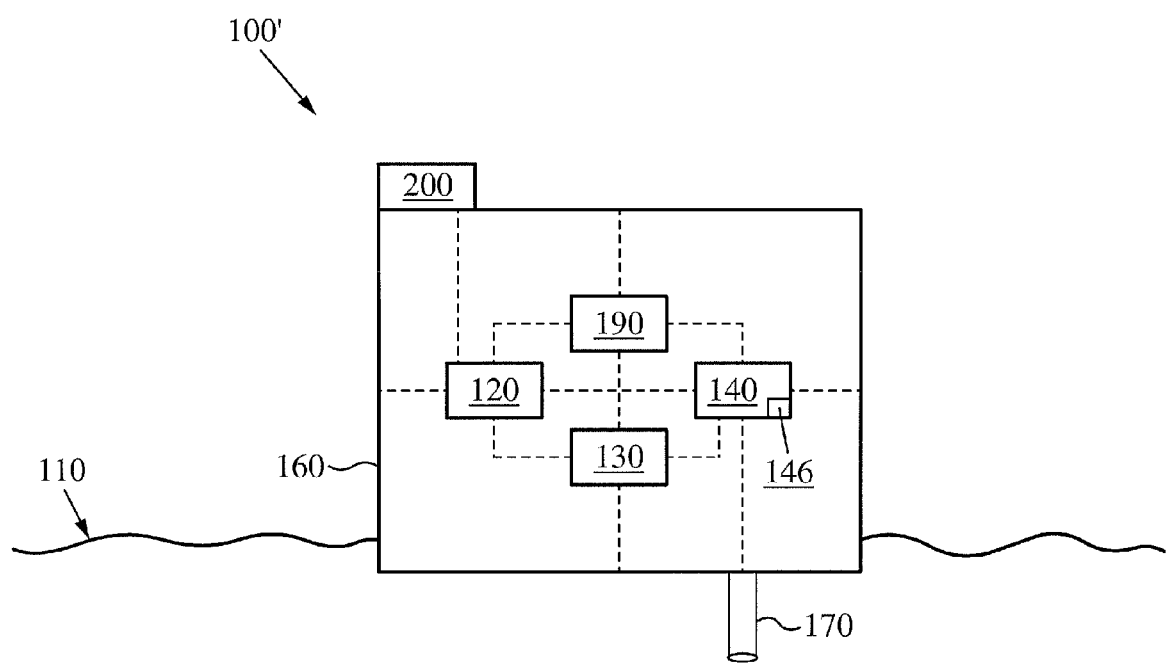
FIG. 2 is a schematic drawing of a further embodiment of the present invention, with the floatable automatic system of FIG. 1 having additional optional features.
Figure 3B:
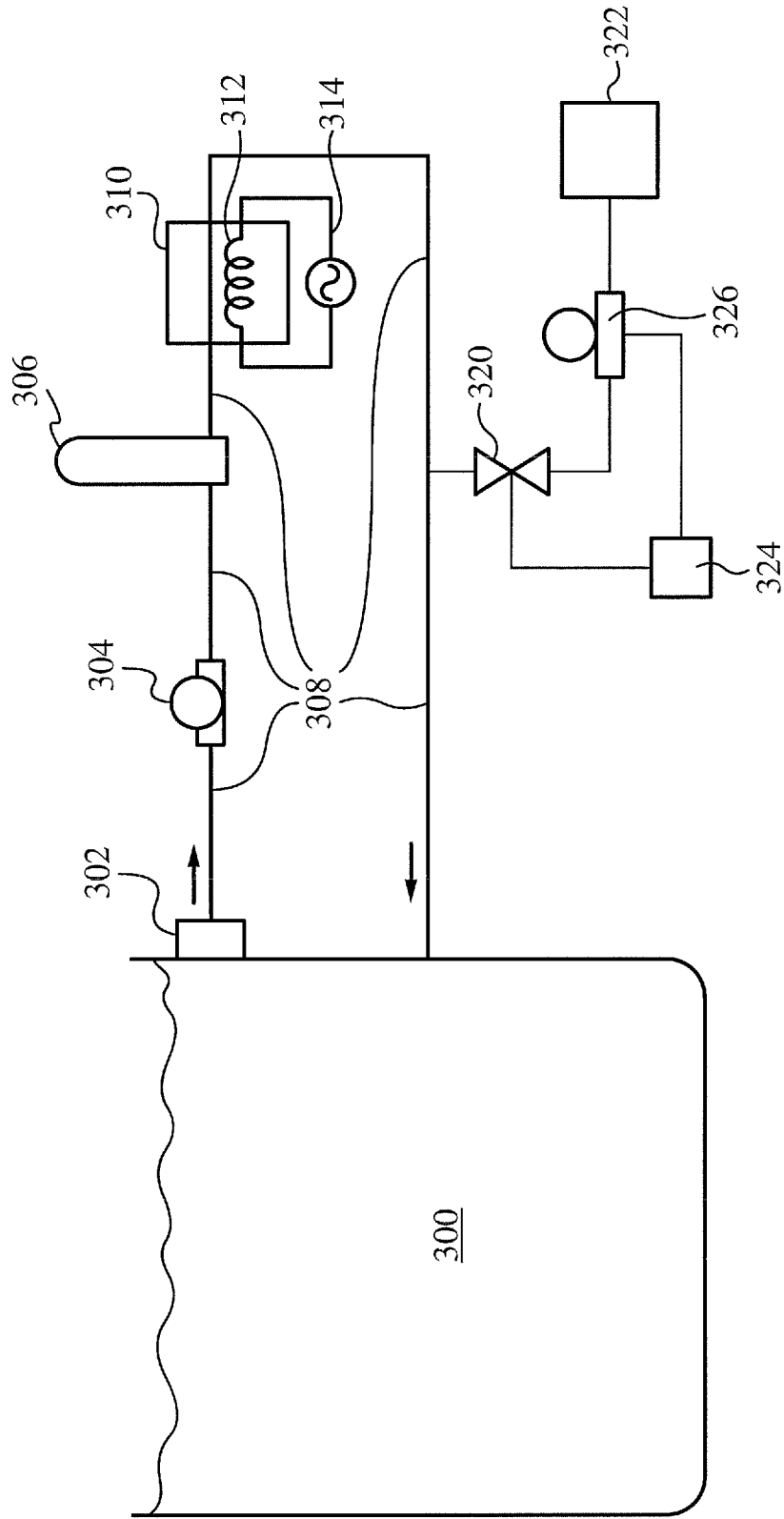
FIG. 3B is a schematic drawing of an embodiment of the present invention, with a chemical delivery system for a pool, hot tub or spa.
Figure 3C:
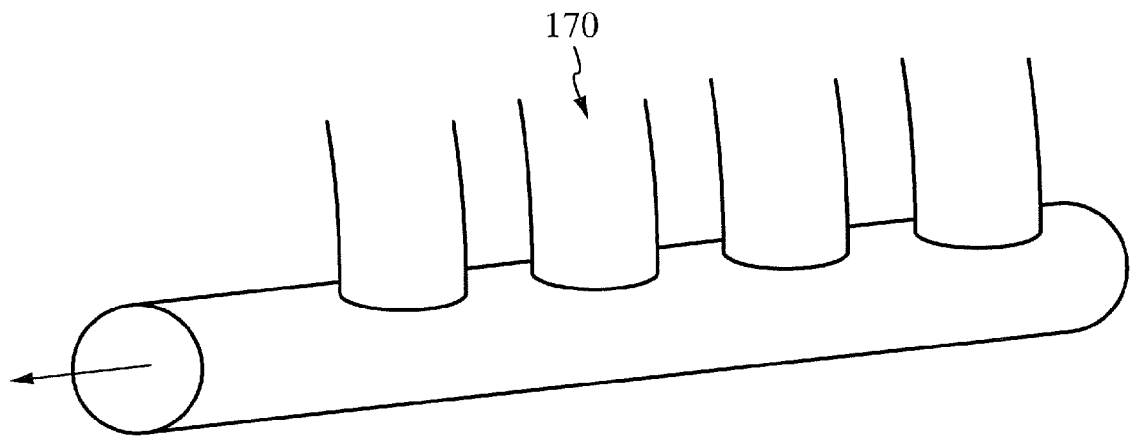
FIGS. 3C and 3D are schematic drawings of two embodiments for a manifold to add chemicals to a pool, hot tub or spa.
Figure 3D:
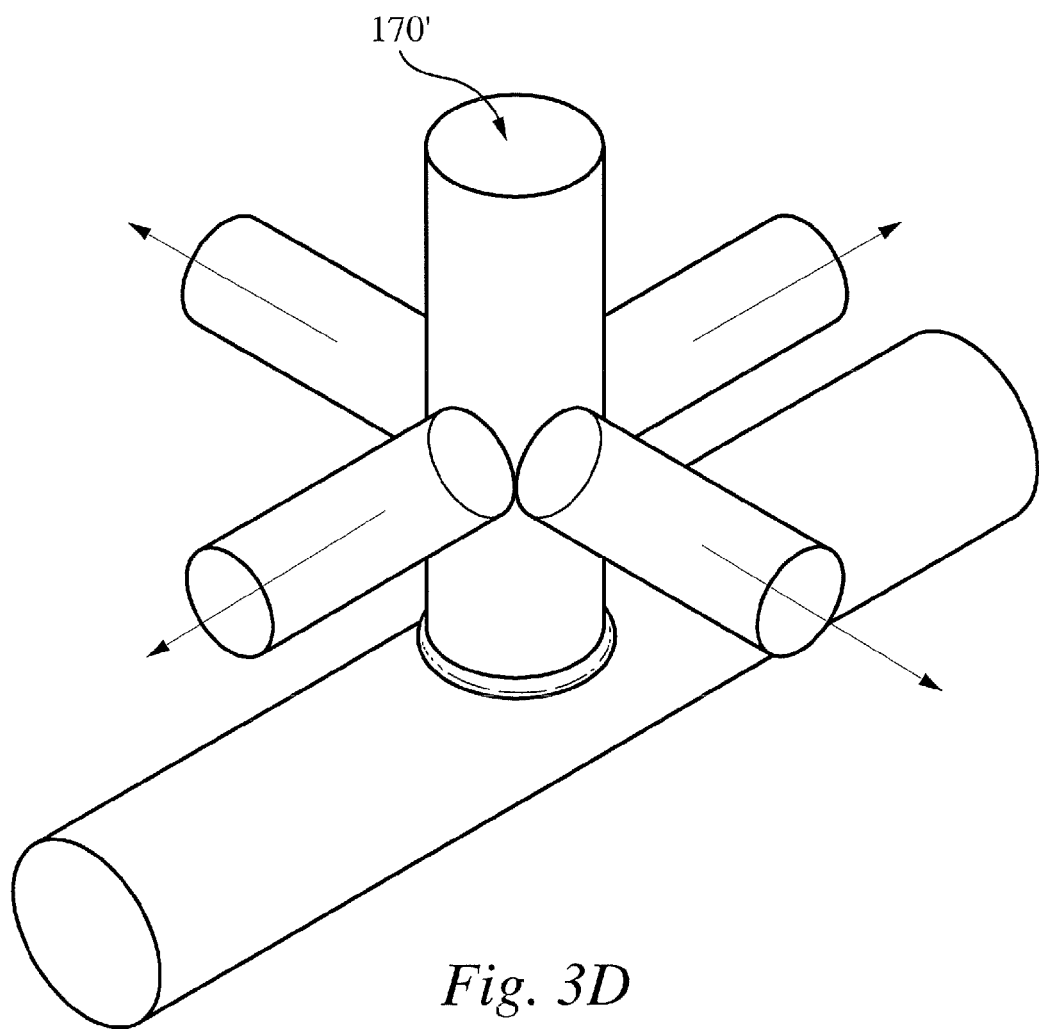

FIG. 3B shows the present invention in conjunction with a chemical delivery system to maintain or restore chemical balance to the pool, hot tub or spa. A valve 320 is coupled into the pipe 308. Preferably, the valve 320 is coupled into the return portion of the pipe 308, but can be included at any position. A chemical to be added is stored in a supply vessel 322. A chemical addition control circuit 324 receives a control signal from the control circuit 140 (FIG. 1 or FIG. 2). Upon receipt of the control signal, the valve 320 opens to allow an amount of chemical in the supply vessel 322 to enter the pipe 308. In certain circumstances, the flow of water through the pipe 308 can be sufficient to draw the chemical from the supply vessel 322 into the pipe 308. Alternatively, the storage vessel 322 can be positioned higher than the pipe 308 to utilize pressure from gravity to induce the chemical to flow from the storage vessel 322 into the pipe 308. If additional pressure is needed, an optional pump 326 can be inserted between the valve 320 and the storage vessel 322 to induce addition of the chemical into the pipe 308. The optional pump 326 also operates under control of the chemical addition control circuit 324. If more than one chemical needs to be added, a manifold 170/170' such as shown in FIG. 3C or 3D can be used for each chemical. Each chemical would have its own storage vessel 322 and valve 320 to feed a unique input to the manifold 170/170'.

FIG. 2 shows an alternative embodiment of the present invention, with the floatable automatic system 100 of FIG. 1 having optional features. As used throughout this document, similar numbered components have similar functions. FIG. 2 illustrates the floatable automatic system 100' having the sensor 120, the control circuit 140, and the floatable housing 160. The system 100' further comprises a timer 190 coupled to at least one of the sensor 120, the control circuit 140, and the housing 160. Preferably, the timer 190 is configured to provide a time stamp to the sensor 120 while the sensor 120 determines chemistry information for the body of water 110. Preferably, the time stamp and chemistry information are coupled as inputs to the control circuit 140. The time stamp and chemistry information can be coupled to the control circuit 140. Therefore, the floatable automatic system 100' can provide chemistry information for the body of water 110, with time stamps. The control circuit 140 further comprises an instruction 146 configured to instruct the control circuit 140 how to process chemistry information.

Still referring to FIG. 2, the floatable system 100' further comprises a memory 130 configured for storing chemistry information and coupled to at least one of the sensor 120, the control circuit 140, and the housing 160. Preferably, the memory 130 is an EPROM, PROM, ROM or Flash memory chip. It will be apparent that the memory 130 and the instruction 146 can be integrally formed in a single integrated circuit. As shown in FIG. 2, in one embodiment of the invention, the system 100' further comprises a optional chemistry display panel 200 coupled to the sensor 120. In this case, the sensor 120 is configured to communicate chemistry information to the chemistry display panel 200. The chemistry information can be displayed continuously and immediately as available. Alternatively, the chemistry information can be displayed at predetermined intervals. It will be apparent that the predetermined intervals can be fixed or programmable.

Figure 4:
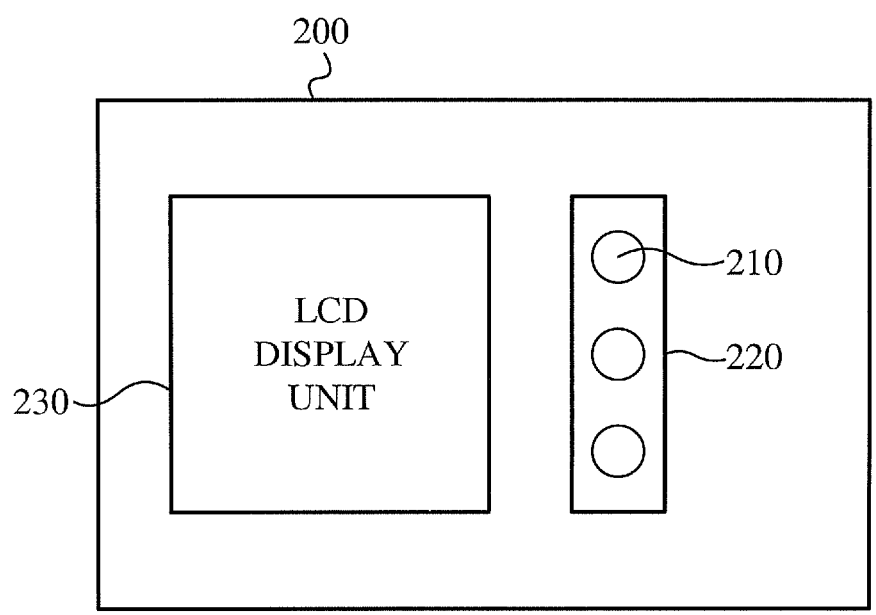
FIG. 4 is a schematic drawing of the chemistry display panel of the system of FIG. 2, with a LCD display unit and a plurality of light indicators.

In the preferred embodiment, as shown in FIG. 4, the chemistry display panel 200 further comprises an indicator 210. The indicator 210 is configured to indicate a status of the body of water 110 based on chemistry information processed by the control circuit 120 (FIGS. 1 and 2). Referring back to FIG. 4, the indicator 210 is preferably a light indicator. Preferably, the chemistry display panel 200 comprises a plurality of light indicators 220, which include a green light indicator, a yellow light indicator, and a red light indicator. Preferably, the color of a light indicator represents the status for the body of water 110 (FIGS. 1 and 2). The green light indicator indicates a safe status, the yellow light indicator indicates a cautionary status, and the red light indicator indicates an unsafe and/or unbalanced status. The safe status for the body of water 110 means that the body of water 110 is balanced and safe to swim. It will be apparent that two thresholds are used to establish the cautionary status and the unsafe status indications. The cautionary status for the body of water 110 means that the chemistry information of the body of water 110 is past a first programmable threshold. The unsafe status for the body of water 110 means that a second programmable threshold is met. Preferably, the unsafe status means the body of water 110 is out of balance and unsafe to enter. Preferably, the unsafe status also indicates that a responsive action is desired to balance the body of water 110, so that the body of water 110 is safe for the intended purpose. The plurality of light indicators 220 is advantageous in its simplicity and clarity in providing an accurate current status of the body of water 110 (FIGS. 1 and 2).

In another alternative embodiment, the indicator 210 (FIG. 4) is an audible indicator. The audible indicator is configured to indicate a status for the body of water 110. As described previously, preferably, the status for the body of water 110 is one of three statuses, namely the safe status, the cautionary status, and the unsafe status. The audible indicator is one of a siren, a beeper, a whistle, a horn, a clicker, and a tonal unit. Preferably, the audible indicator has a text to speech capability, similar to computer-generated speech, so that an individual can listen to the status for the body of water 110, rather than having to look at the chemical display panel 200 (FIGS. 2 and 4). It will be appreciated by those skilled in the art that the indicator 210 (FIG. 4) can take on many different shapes and forms, singly or in a variety of combinations. For instance, the indicator 210 can be both a light indicator and an audible indicator.

Figure 5:
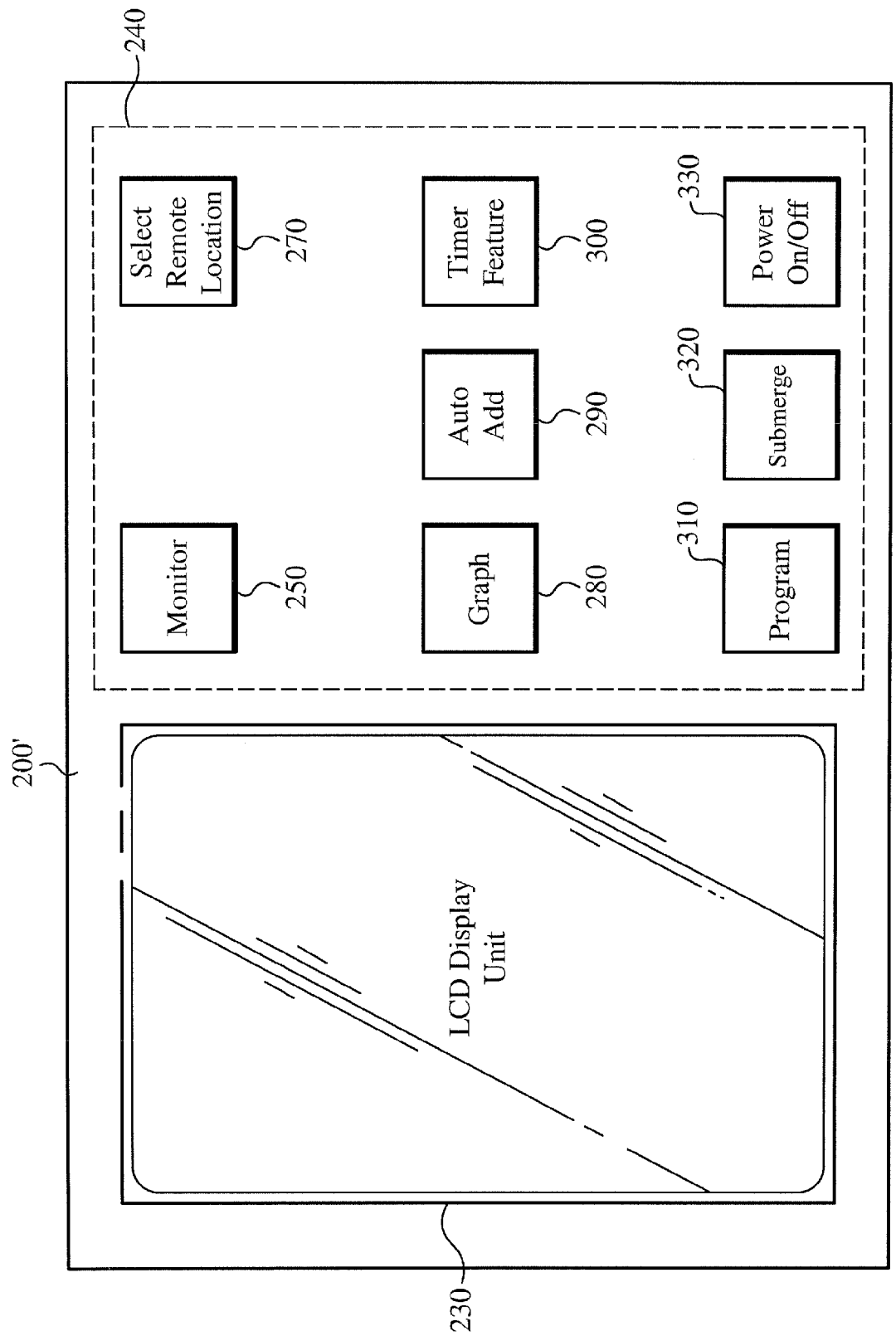
FIG. 5 is a schematic drawing of the chemistry display panel of the system of FIG. 2, with a LCD display unit and a button panel.

Turning to FIG. 5, in yet another embodiment of the present invention, the chemistry display panel 200' further comprises a LCD display unit 230 and an optional button panel 240. It will be appreciated by those skilled in the art that the button panel 240 can include one or more buttons in a multitude of shapes, sizes, and forms, and that the button panel 240 of FIG. 5 is for illustrative purposes only. The button panel 240 comprises of eight buttons in total, namely a Monitor button 250, a Select Remote Location button 270, a Graph button 280, an Auto Add button 290, a Timer Feature button 300, a Program button 310, a Submerge button 320, and a Power On/Off button 330.

When the Monitor button 250 is pressed, the system 100' (FIG. 2) will begin monitoring the body of water 110 (FIG. 2). The Select Remote Location button 270 selects a remote location to which the chemistry information will be sent. The remote location is preferably a personal digital assistant (PDA), a custom sign, a computer, a satellite, a wireless device, a phone, a USB port, a pager, or a device configured to add chemicals to the body of water 110 (FIG. 2). However, it will be appreciated by those skilled in the art that the remote location can be any location, including locations on land and at sea, to which chemistry information will be sent. Preferably, the sensor 120 (FIGS. 1 and 2) is configured to communicate chemistry information of the body of water 110 (FIGS. 1 and 2) to the remote location. The sensor 120 (FIGS. 1 and 2) is further configured to communicate chemistry information to the remote location through at least one of a wireless connection, a cellular connection, a wired connection, an optical connection, an infrared connection, and a custom radio interface connection.

Still referring to the button panel 240 of FIG. 5, when the Graph button 280 is pressed, a graphing feature of the system 100' (FIG. 2) is activated. Preferably, the LCD display unit 230 will provide a graph with Cartesian coordinates having at least an x-axis and a y-axis. Based on the time stamp provided by the timer 190 (FIG. 2) and chemistry information processed by the control circuit 140 (FIG. 2), the system 100' can provide a graph to be displayed by the LCD display unit 230, the graph having its x-axis labeled "Time" and its y-axis labeled "Chemical Content." The graph can thus show the levels of a particular chemical component of the body of water 110 (FIG. 2) at different time intervals. It will be appreciated by those skilled in the art that the graph can take on many forms, shapes, and sizes, including but not limited to a pie graph, a bar graph, a line graph, and the like. Furthermore, it will be appreciated by those skilled in the art that in the preferred embodiment, the system 100' can monitor more than one chemical component for the body of water 110 and therefore the system 100' can display more than one graph at a time. Preferably, the LCD display unit 230 displays a plurality of line graphs, each line representing a chemical component for the body of water 110. For instance, one graph each can track the chlorine, bromine, and the pH level content of the body of water 110 all in one time. It will be further appreciated by those skilled in the art that the system 100' can monitor chemistry information for the body of water 110 continually or at different intervals.

Still referring to FIG. 5, the Auto Add button 290 is configured such that when it is pressed, the system 100' (FIG. 2) automatically provides a signal to add a particular chemical into the body of water 110 upon command. This automatic feature will be discussed at greater length later in this document. The Timer Feature button 300 activates the timer 190 (FIG. 2). The Program button 310 allows for the system 100' to be programmed with a variety of functions and commands. For instance, the Program button 310 can set the programmable threshold of chemistry information for the body of water 110 as previously discussed. The Program button 310 can further program the system 100' (FIG. 2) to obtain a sample from the body of water 110 at specific time intervals and at specific locations. The Submerge button 320 enables the system 100' to sink to a specified programmable water depth. Finally, the Power On/Off button 330 when pressed can turn on or shut off a power supply (not shown) to the system 100'. It will be appreciated by those skilled in the art that the power supply to the system 100' can be of any power source, including but not limited to a battery, a solar cell, or a low voltage power source.

Figure 6:
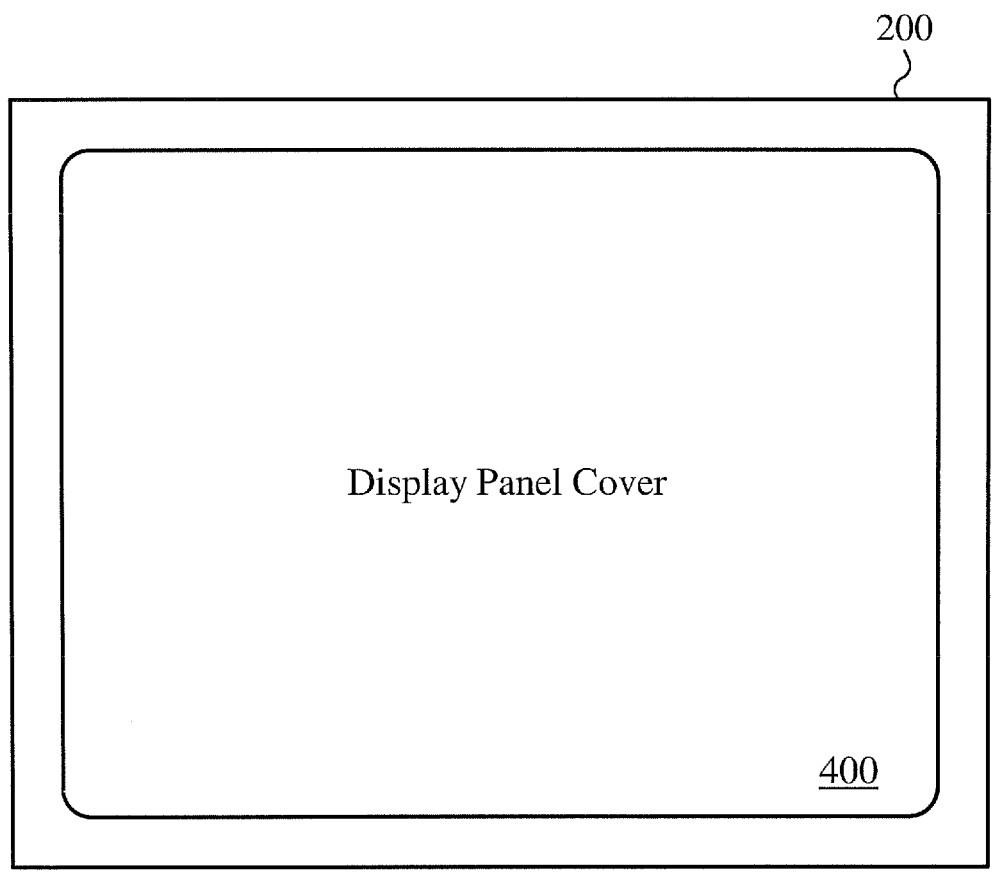
FIG. 6 is a schematic drawing of the chemistry display panel of the system of FIG. 2 with a panel cover in a closed position.

Turning now to FIG. 6, in another embodiment, the chemistry display panel 200 further comprises a display panel cover 400 configured to protect the chemistry display panel 200. The display panel cover 400 is configured to protect the chemistry display panel 200 from ultraviolet radiation, weather elements, insects, animals, water, and the like. It will be appreciated by those skilled in the art that the display panel cover 400 can be made of any protective material, including but not limited to plastic and metal. The display panel cover 400 can also be of any color or texture. Preferably, the display panel cover 400 is waterproof and clear, so that the chemistry display panel 200 can be easily viewed without moving the display panel cover 400 from a closed position, as shown in FIG. 6.

One of the benefits stemming from the automatic feature of the system 100/100' is that the system 100/100' (FIGS. 1 and 2) can provide up-to-date chemistry information for the body of water 110 without supervision. For instance, in a health spa, the number of people using the spa can fluctuate dramatically from hour to hour. If many people enter into the health spa at one given hour (such as lunch hour), then the chemistry of the spa is apt to change, and sometimes it changes drastically such that the spa becomes unsafe to enter. If the system 100/100' is programmed with one or more programmable thresholds to monitor chemistry information of the spa, then the system 100/100' can alert a spa employee when the spa is past the cautionary threshold and approaching the unsafe threshold. The system 100/100' can also indicate to the spa employee when a chemical needs to be released to balance the water in the spa. In certain embodiments, the system 100/100' can indicate to the spa employee which chemical(s) and how much of the chemical(s) must be added.

In yet another embodiment of the present invention, the floatable automatic system 100/100' (FIGS. 1 and 2) is configured to sink or float to at least one predetermined water depth measured from the surface of the body of water 110. Thus, the floatable automatic system 100/100' is configured to submerge in the body of water 110 so that chemistry information for the body of water 110 can be monitored at different water depths. Ideally, the floatable automatic system 100/100' provides the water depth, chemical information (via the sensor 120 (FIG. 2)) and exact time of the sampling (via the timer 180 (FIG. 2)). This compilation of information can then be sent to the remote location through a connection as described previously. The Submerge button 320 (FIG. 5) and the Program button 310 are preferably used to accomplish these tasks.

Figure 7:
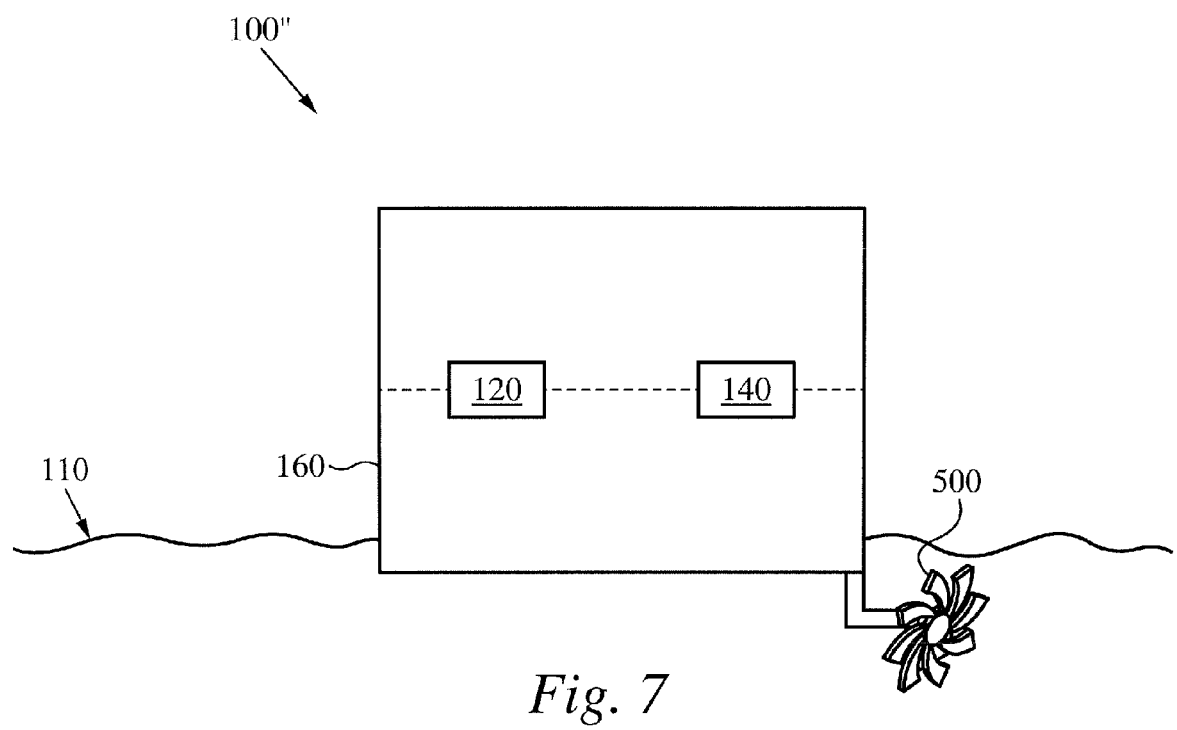
FIG. 7 is a schematic drawing of the floatable automatic system of FIG. 1, with an optional actuator.

Turning to FIG. 7, in an alternative embodiment of the present invention, the floatable system 100" further comprises an actuator 500 to relocate the system 100" to at least one predetermined geographic location of the body of water 110. As throughout this document, like numbered components have like functions. It will be appreciated by those skilled in the art that the actuator 500 can be in a number of forms, shapes, and sizes. For instance, the actuator 500 can be a motorized propeller or can be a burst of water jet stream. FIG. 7 shows a motorized propeller for the actuator 500 for illustrative purposes only. In yet another embodiment, the floatable automatic system 100 (FIG. 1) is configured to be tethered.

Figure 8:
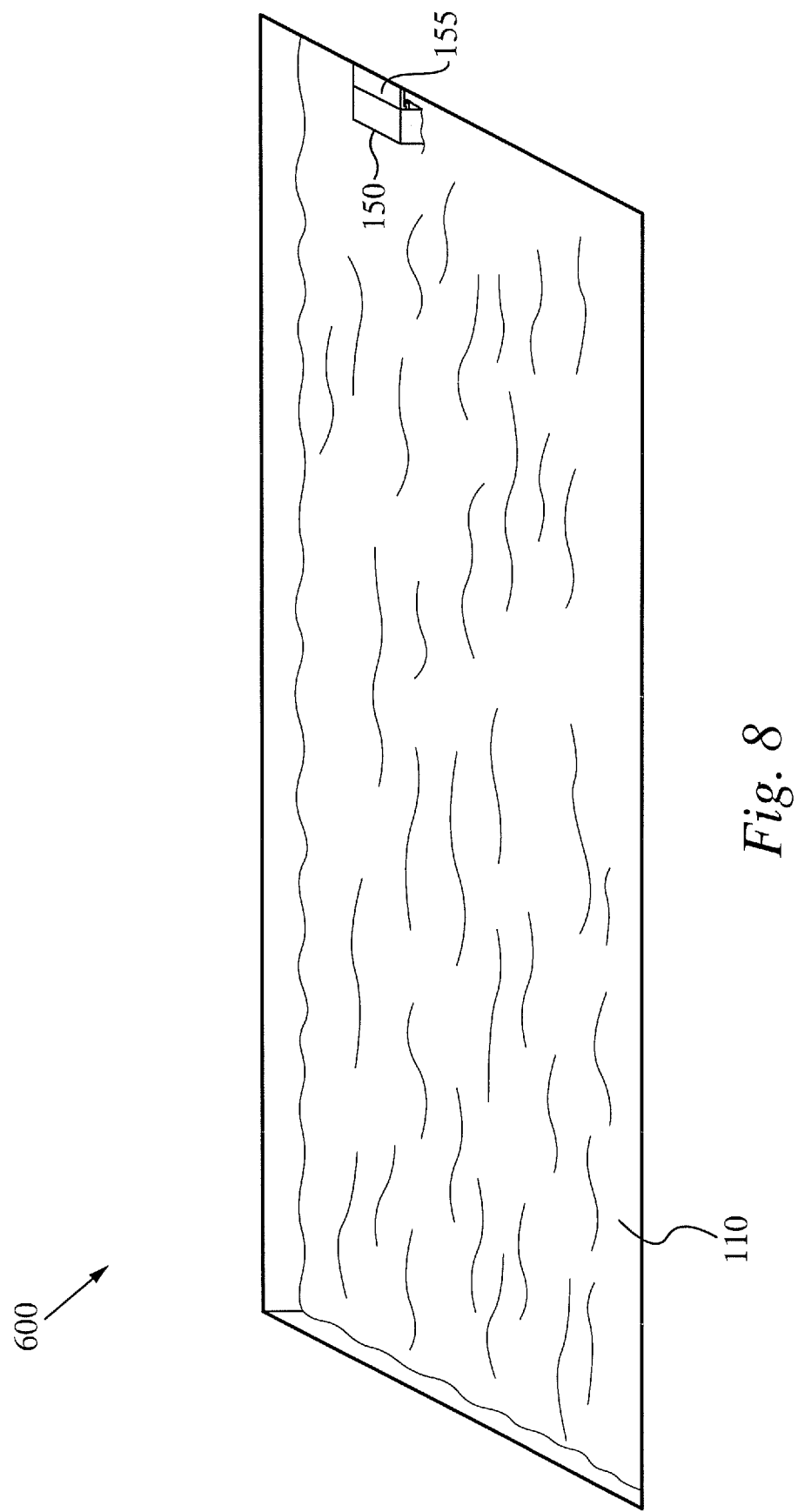
FIG. 8 is a schematic drawing of an embodiment of a mountable automatic system with a mountable housing.
Figure 9:
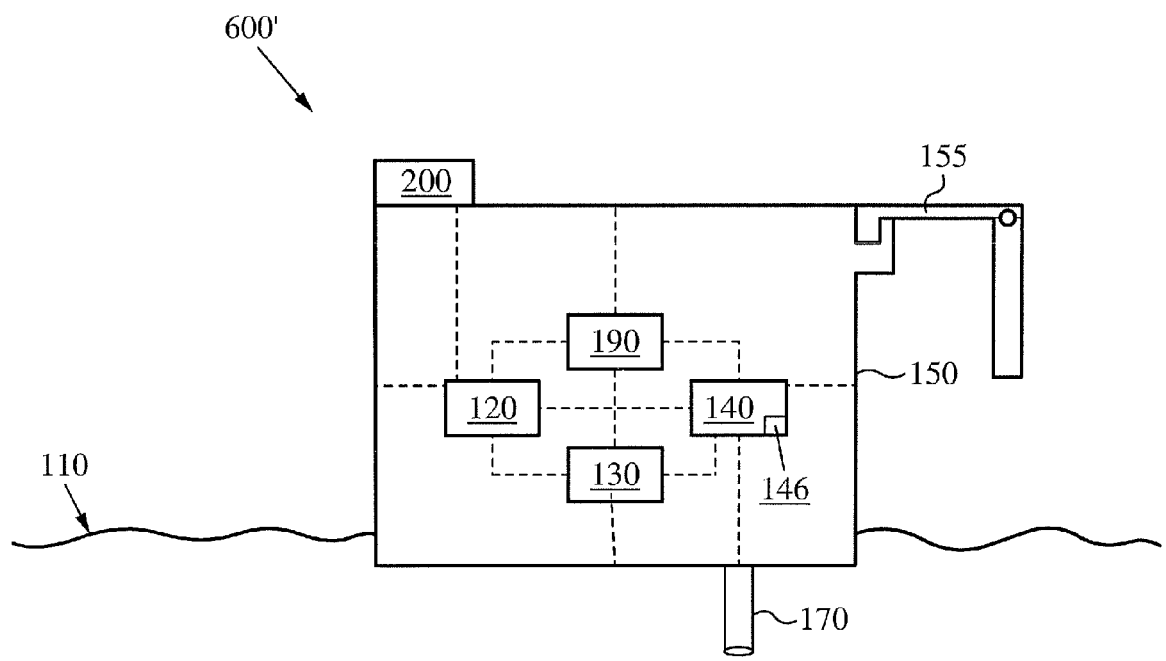
FIG. 9 is a schematic drawing of an alternative embodiment of the mountable automatic system of FIG. 8, with optional features.

Turning to FIG. 8, in an alternative embodiment, the automatic system 600 is a mountable automatic system, having a mountable housing 150. It will be understood by one of ordinary skill in the art that the automatic system can be mounted to an edge or wall of a pool, hot tub or spa or can be integrally formed within a wall. Likewise, the automatic system 600 can be mounted to the circulation pump and filter system of the pool, hot tub or spa or within the skimmer enclosure. FIGS. 8 and 9 are drawings of the mountable automatic system 600/600'. FIG. 8 is the preferred embodiment of the mountable automatic system 600. FIG. 9 is an alternative embodiment of the mountable automatic system 600' with optional features. As throughout this document, like numbered components have like functions.

As shown in FIGS. 8 and 9, the mountable housing 150 comprises of a bracket 155 for mounting to a wall or edge of the pool, hot tub or spa. Preferably, the mountable housing 150 is mounted within the skimmer 302 (FIGS. 3A and 3B) to avoid interfering with enjoyment of the pool, hot tub or spa. However, such a mountable housing 150 could comprise instead of a cup-like suction or a Velcro attachment configured to mount to the structure containing the body of water 110. It will be appreciated by those skilled in the art that the mountable housing 150 can be configured to attach to any surface, edge, or physical feature of the body of water 110, including but not limited to a bottom surface of the body of water 110.

Figure 10A:
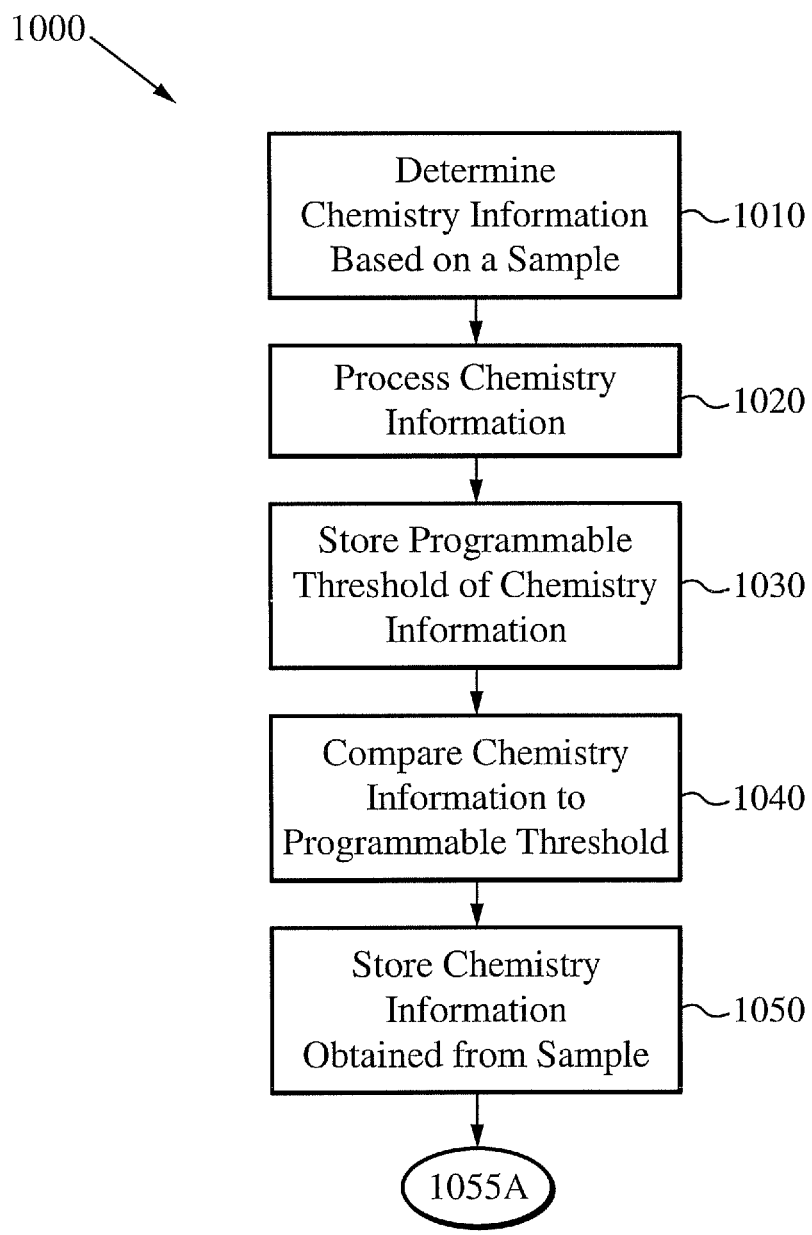
FIG. 10A is a flow chart of the steps of a preferred method of automatically monitoring chemistry information of a body of water.

Now referring to FIG. 10A, the present invention includes a method of automatically monitoring chemistry information of a body of water 1000. The method 1000 comprises two steps. The first step is the step of determining chemistry information based on a sample obtained from the body of water 1010. The second step is the step of processing chemistry information 1020. In another embodiment of the invention, the method 1000 further comprises two additional steps, namely, the step of storing a programmable threshold of chemistry information 1030 and the step of comparing chemistry information to the programmable threshold 1040. In an alternative embodiment, the method 1000 further comprises the step of storing chemistry information of the sample 1050. At the step 1050, the method 1000 can stop at a step 1055A.

Figure 10B:
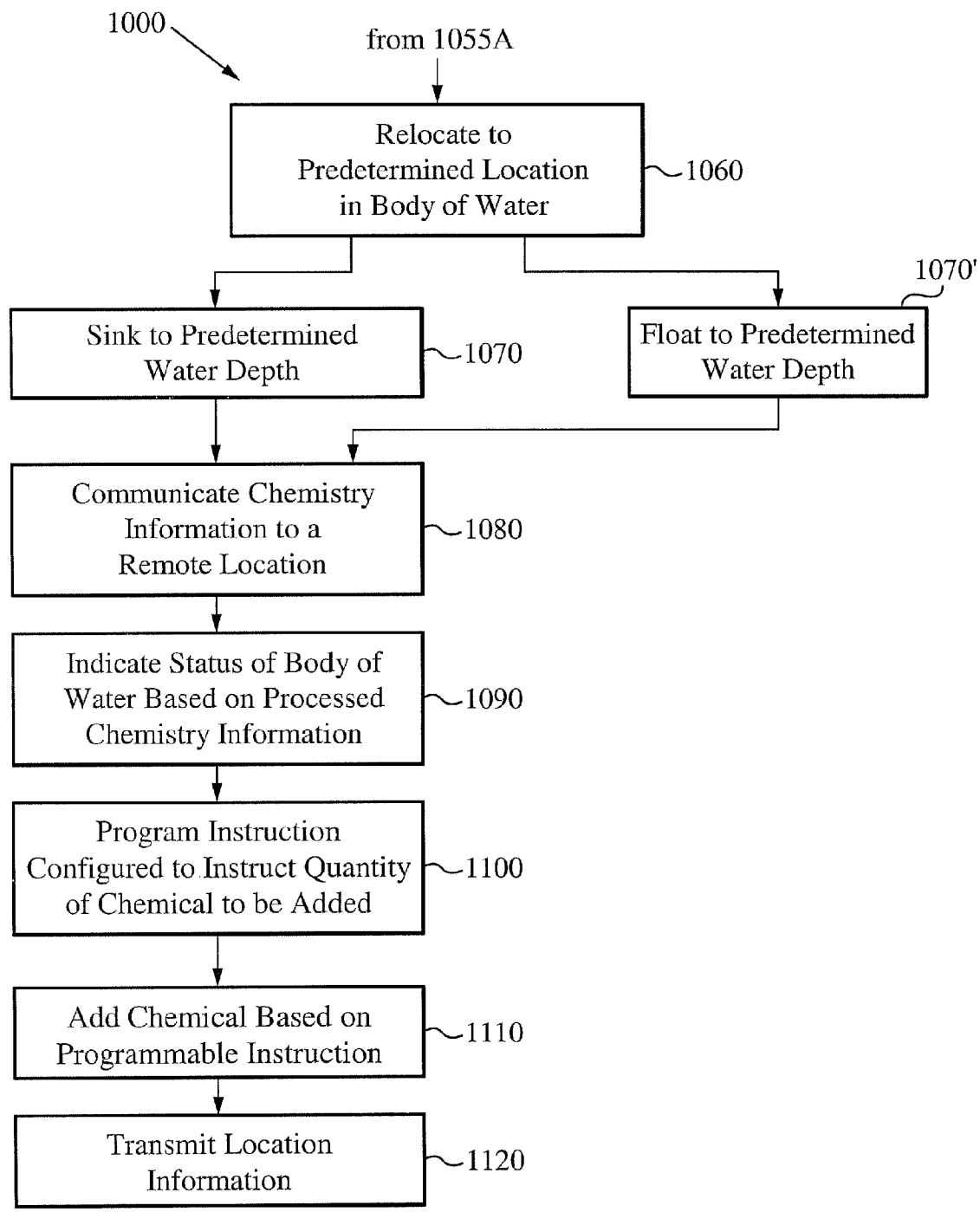
FIG. 10B is a flow chart of an alternative embodiment for the method of automatically monitoring chemistry information of the body of water. The flow chart in FIG. 10B depicts steps which represent an optional path, beginning with the last step depicted in FIG. 10A.

Alternatively, in FIG. 10B, the method 1000 can continue with further optional steps beginning with the step 1055A from FIG. 10A. In FIG. 10B, the method 1000 further comprises the step of relocating to a predetermined location in the body of water 1060. The method 1000 further comprises the step of sinking to a predetermined water depth measured from a surface of the body of water 1070. Alternatively, the method 1000 further comprises the step of floating to a predetermined water depth measured from a surface of the body of water 1070'. An alternative embodiment includes the method 1000 further comprising the step of communicating chemistry information to a remote location 1080.

Preferably, the method 1000 further comprises the step of indicating a status of the body of water based on processed chemistry information 1090. Preferably, the method 1000 also comprises the step of programming an instruction configured to instruct the quantity of a chemical to be added to the body of water once a programmable threshold has been met 1100. Alternatively, the method 1000 further comprises the step of adding a chemical to the body of water based on a programmable instruction 1110.

The present invention further includes an automatic system for monitoring chemistry information of a body of water. The system comprises means for determining chemistry information based on a sample obtained from the body of water and means for processing chemistry information. The system can further comprise means for storing a programmable threshold of chemistry information and means for comparing chemistry information based on the sample to the programmable threshold. In an alternative embodiment, the system further comprises means for storing chemistry information. Preferably, the system is configured to operate continually while the system is powered on. Optionally, the system further comprises means for relocating to a predetermined location of the body of water. Also, the system further comprises means for sinking or, alternatively, means for floating to a predetermined water depth measured from a surface of the body of water. The system further comprises means for communicating chemistry information to a remote location, where the remote location is one of a personal digital assistant (PDA), a custom sign, a computer, a satellite, a wireless device, a phone, a USB port, a pager, and a device configured to add chemicals to the body of water. The system further comprises means for indicating a status for the body of water based on processed chemistry information, and optionally it further comprises means for adding a chemical to the body of water based on the status of the body of water.

Figure 11:
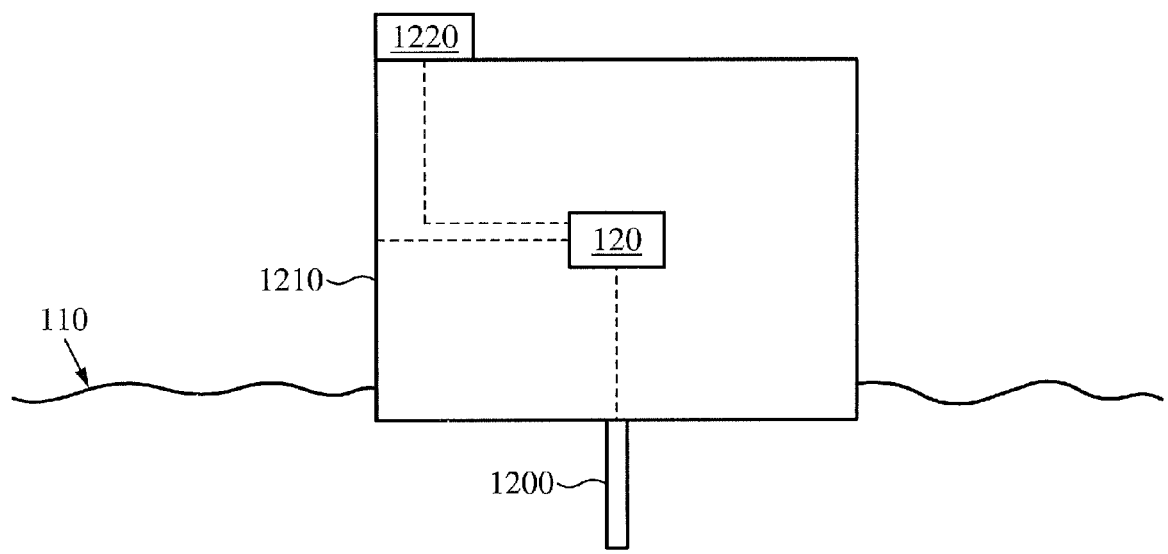
FIG. 11 is a schematic drawing of an alternative embodiment of a system for sensing chemistry information of a body of water, including an automatic sensor, a retrieval element, a housing, and an optional LCD display unit.

Now referring to FIG. 11, the present invention further includes an automatic sensor 120 for providing chemistry information for a body of water 110. The sensor 120 is configured to couple to a retrieval element 1200 and a housing 1210. The retrieval element 1200 is configured to retrieve a sample from the body of water 110. The sensor 120 is configured to couple to a microprocessor (not shown) to process chemistry information based on the sample from the body of water 110. Preferably, the sensor 120 provides chemistry information of the body of water 110. The housing 1210 is one of a floatable housing, a skimmable housing, a tetherable housing, and a mountable housing. In another embodiment, the sensor 120 communicates chemistry information via a display 1220. Preferably, the display 1220 is a sensor-mounted LCD display unit. In yet another embodiment, the sensor 120 communicates chemistry information to a remote location.

Figure 12:
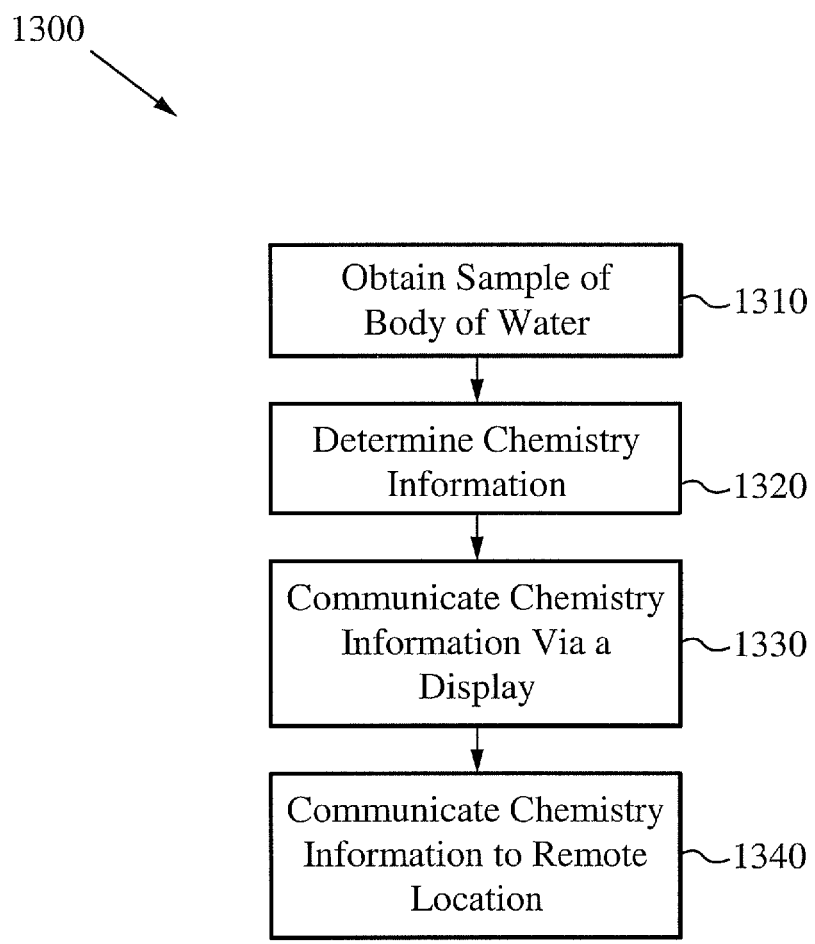
FIG. 12 is a flow chart depicting the steps of a method of providing chemistry information of a body of water.

Now referring to FIG. 12, the present invention also includes a method of providing chemistry information of a body of water 1300. The method 1300 comprises two steps, namely, the step of obtaining a sample of the body of water 1310 and the step of determining chemistry information 1320. The method 1300 can further comprise the optional step of communicating chemistry information via a display 1330. Also, the method 1300 may comprise the additional step of communicating chemistry information to a remote location 1340.

Figure 13:
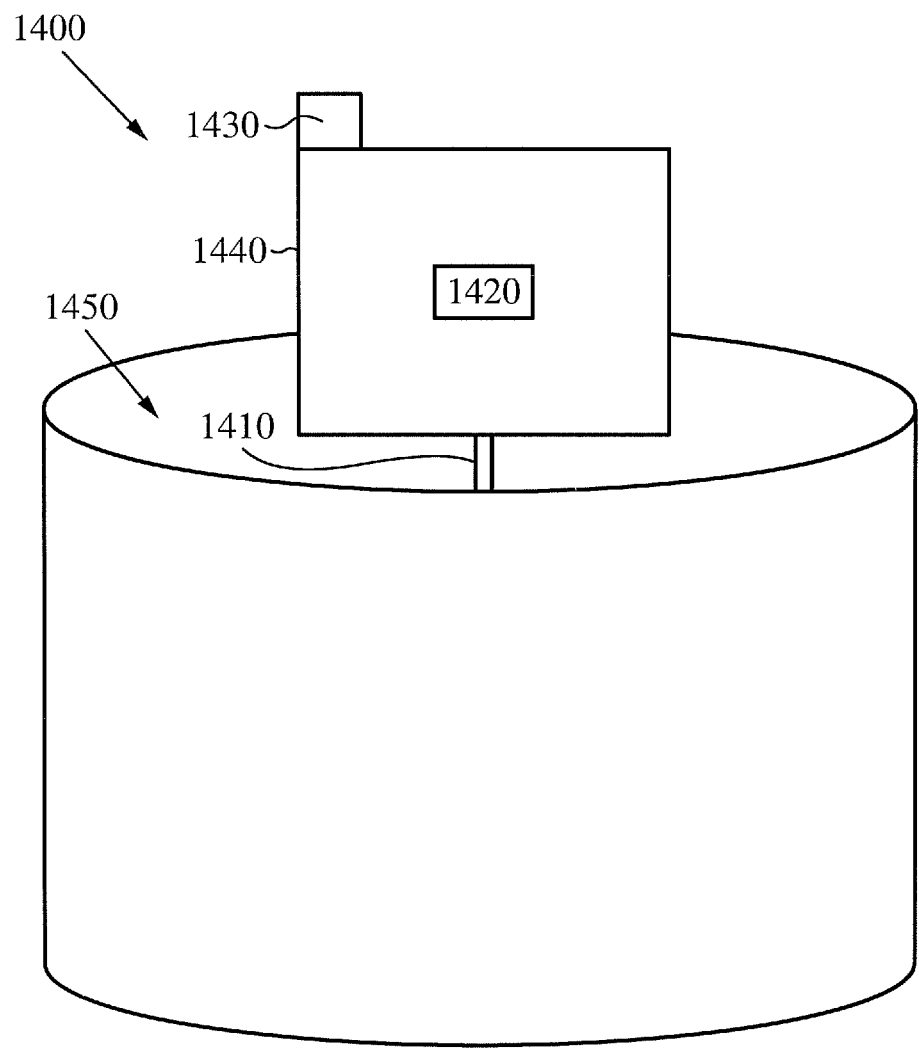
FIG. 13 is a schematic drawing of an embodiment of an automatic system for monitoring chemistry information for hot tub water.

The invention further includes an embodiment of an automatic system for monitoring chemistry information for hot tub water 1400, as shown in FIG. 13. The system 1400 comprises four elements, namely, a retrieval element 1410, a sensor 1420, a display 1430, and a housing 1440. The retrieval element 1410 is configured to obtain a sample from hot tub water 1450. Preferably, the retrieval element 1410 is floatable. The sensor 1420 is coupled to the retrieval element 1410 and is configured for determining chemistry information from the sample obtained from hot tub water 1450. The display 1430 is coupled to the sensor 1420 and is for displaying chemistry information. Finally, the housing 1440 is coupled to one of the retrieval element 1410, the sensor 1420, and the display 1430. In one embodiment, the housing 1440 is a floatable housing. Alternatively, the housing 1440 is a mountable housing. Preferably, the display 1430 displays an alert if a predetermined threshold for chemistry information has been met. Preferably, the display 1430 further displays an instruction of what chemical must be added once the predetermined threshold for chemistry information has been met.

Figure 14:
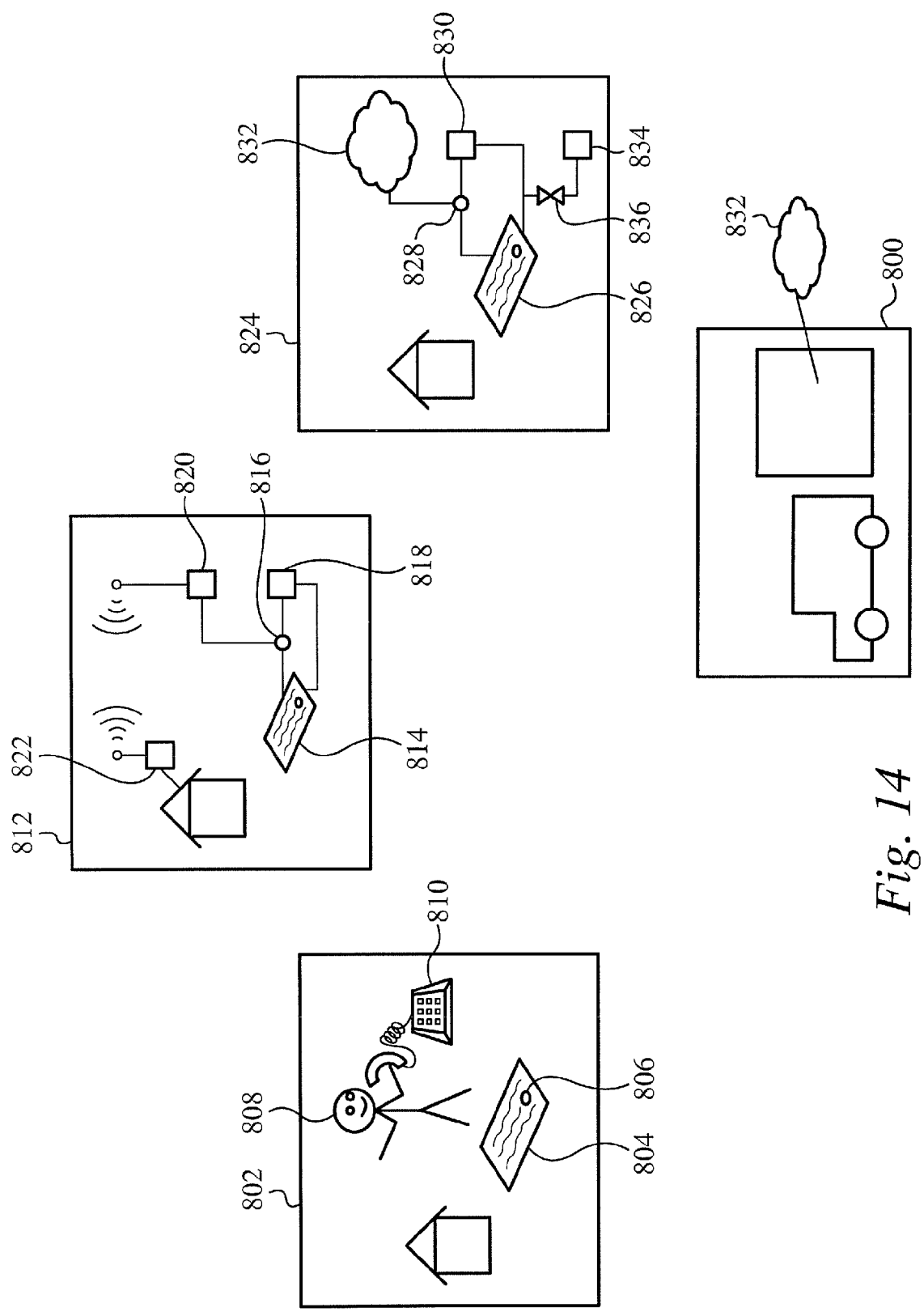
FIG. 14 is a schematic drawing showing embodiments of the invention in use in a networked system.

FIG. 14 shows one example of many potential configurations of the present invention in use in a networked system. A system operator 800, such as a pool service company, maintains pools, hot tubs and/or spas for a plurality of customers. At a first customer site 802, there is a swimming pool 804 with a floating system 806 such as described in detail above. When the floating system 806 provides an indication that the water in the pool is out of balance, the pool owner 808 uses their telephone 810 to notify the system operator 800. The system operator 800 will dispatch a service technician to the first customer site 802.

At a second customer site 812, there is a hot tub 814 with a mounted system 816 such as described in detail above. The mounted system 816 can be mounted to a wall of the hot tub 814, within a skimmer or in the recirculation system 818. A wireless communication circuit 820 is coupled to the mounted system 816. Upon sensing an unbalanced condition in the water of the hot tub 814, the mounted system 816 signals the wireless communication circuit 820 to transmit the unbalanced condition. The wireless communication circuit 820 can communicate via radio, cellular, infrared, Bluetooth or any other convenient protocol. A wireless receiver 822 is positioned to receive a transmission from the wireless communication circuit 820 and to transmit information regarding condition of the hot tub 814 to the system operator 800, remotely. The transmission to the system operator 800 can be modem, either hard wired or by cellular, but is preferably via the internet either using an internal modem, or a broadband internet connection. The system operator 800 will dispatch a service technician to the second customer site 812.

At a third customer site 824, there is a pool 826 with a mounted system 828 such as described in detail above. The mounted system 828 is shown mounted in the recirculation system 830. The mounted system 828 includes a direct link to the internet 832 via its own circuit and broadband connection. A storage vessel 834 and a valve 836 are configured to automatically add a chemical. Upon sensing an unbalanced condition in the water of the pool 826, the mounted system 828 signals valve 836 to open and add a predetermined amount of the chemical. In addition, the mounted system 828 sends that information to the system operator 800 via the internet 832. The system operator 800 tracks the amount of chemical added to the pool 826. The system operator 800 will dispatch a service technician to the third customer site 824 to replenish the chemical in the storage vessel 834 when it is determined that the vessel is empty or near empty in response to chemical being added. Alternatively, the storage vessel 834 can include a fill level gauge which is coupled to provide its condition to the mounted system 828. That information can also be communicated via the internet to the system operator 800.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications can be made in the embodiment chosen for illustration without departing from the spirit and scope of the invention. Specifically, it will be apparent to one of ordinary skill in the art that the method and system of the present invention could be implemented in several different ways and have several different appearances.

What is claimed is:

1. An automatic system for monitoring chemistry information for a body of water, comprising:
    a. a housing;
    b. at least one sensor coupled to the housing, the at least one sensor configured to determine chemistry information for the body of water; and
    c. a control circuit coupled to the at least one sensor, the control circuit is programmable with at least one acceptable threshold level of chemical composition for the body of water, wherein the system is configured to suggest the at least one acceptable threshold level specifically for the body of water in response to a parameter of a volume and a type of the body of water entered.

2. The automatic system of claim 1, wherein the control circuit compares the chemistry information determined by the at least one sensor to a programmable threshold.

3. The automatic system of claim 2, wherein the threshold represents an acceptable minimum value or maximum value of the chemistry information for the body of the water.

4. The automatic system of claim 1, wherein the chemistry information monitored by the system comprises one of at least one alkalinity, pH level, temperature, calcium hardness, total hardness, dissolved solids, and a sanitizer of the body of water and a combination of at least two thereof.

5. The automatic system of claim 4, wherein the sanitizer is one of chlorine or bromine.

6. The automatic system of claim 1, wherein the system is configured to monitor the chemistry information for the body of water continually while the system is powered on.

7. The automatic system of claim 1, wherein the system further comprises a timer coupled to at least one of the at least one sensor, the control circuit, and the housing.

8. The automatic system of claim 7, wherein the timer is configured to provide a time stamp to the at least one sensor while the at least one sensor determines the chemistry information for the body of water.

9. The automatic system of claim 8, wherein the time stamp and the chemistry information are transmitted to the control circuit.

10. The automatic system of claim 1, wherein the system further comprises a chemistry display panel coupled to the at least one sensor.

11. The automatic system of claim 10, wherein the at least one sensor is configured to communicate the chemistry information to the chemistry display panel during a programmable time interval.

12. The automatic system of claim 10, wherein the chemistry display panel further comprises an indicator configured to indicate a status of the body of water based on the chemistry information processed by the control circuit.

13. The automatic system of claim 12, wherein the indicator is one of a green light indicator for a safe status for the body of water, a yellow light indicator for a cautionary status for the body of water, and a red light indicator for an unsafe status for the body of water.

14. The automatic system of claim 12, wherein the indicator is configured to be audible.

15. The automatic system of claim 1, wherein the at least one sensor is configured to communicate the chemistry information to a remote location.

16. The automatic system of claim 15, wherein the remote location is one of a personal digital assistant (PDA), a custom sign, a computer, a satellite, a wireless device, a phone, a USB port, a pager, and a device configured to add chemicals to the body of water.

17. The automatic system of claim 15, wherein the at least one sensor is configured to communicate the chemistry information to the remote location through at least one of a wireless connection, a cellular connection, a wired connection, an optical connection, an infrared connection, and a custom radio interface connection.

18. The automatic system of claim 1, wherein the system further comprises an antenna coupled to the housing and configured to transmit and receive radio waves.

19. The automatic system of claim 1, the system further comprising a pump system for collecting a sample of the body of water.

20. The automatic system of claim 1, the system further comprising a safety element configured for indicating when the body of water is unsafe.

21. The automatic system of claim 1, wherein the system is at least one of mountable and floatable.

22. The automatic system of claim 1, wherein the system is configured to be tethered.

23. The automatic system of claim 1, wherein the system is further configured to selectively float to at least one predetermined water depth measured from the surface of the body of water.

24. The automatic system of claim 1, wherein the system further comprises an actuator to relocate the system to at least one predetermined location of the body of water.

* * * * *